United States Patent [19]
Rackson

[11] 3,959,882
[45] June 1, 1976

[54] FLUID CONTROL APPARATUS

[76] Inventor: Chester B. Rackson, 22 Orchard Drive, Woodbury, N.Y. 11797

[22] Filed: June 17, 1974

[21] Appl. No.: 479,845

[52] U.S. Cl. ................................. 32/22
[51] Int. Cl.² ............................ A61C 19/02
[58] Field of Search .......................... 32/22

[56] References Cited
UNITED STATES PATENTS

| | | | |
|---|---|---|---|
| 3,568,318 | 3/1971 | Martin | 32/27 |
| 3,732,622 | 5/1973 | Rackson | 32/22 |
| 3,757,421 | 9/1973 | Kraft | 32/22 |
| 3,842,504 | 10/1974 | Ricks | 32/27 |

*Primary Examiner*—Robert Peshock
*Attorney, Agent, or Firm*—Bauer. Amer & King

[57] ABSTRACT

A fluid control apparatus more particularly for use in dental systems and with dental tools and workpieces to enable the finite control, by the operation by hand, of the functions required to be performed by the actuated dental tools and workpieces wherein the control apparatus includes operative elements for selective connection to the actuated dental tools and workpieces.

9 Claims, 4 Drawing Figures

FLUID CONTROL APPARATUS

BACKGROUND OF THE INVENTION

This invention relates to a control apparatus that enables different tools and workpieces to be selectively connected thereto, and by the deployment and manipulation of a portable hand operated control device such tools and workpieces may be selectively actuated and their functions finitely controlled.

In the modern practice of dentistry, the dentist or technician may have a variety of tools and handpieces, sometimes referred to as workpieces, that are available and ready for use with burrs and other working elements affixed thereto for the performance of various desired tasks. The generally accepted method of operation of such dental tools and workpieces has been to connect each of them to a driving apparatus as and when the same is needed and then operate the driving apparatus by toe pressure applied by the dentist to a foot control that rests on the floor.

Although this procedure has been accepted as standard procedure for many years, it has been unsatisfactory. The use of the foot control often requires the dentist to divert his attention from the patient to look for and find the control that is movable about the floor. It requires him to stand off balance on one foot while operating the control with the toe of his other foot. This causes posture and orthopedic problems and oftentimes the dentist finds that it is not easy to manipulate the toe control to effect the finite control of the hand tool or workpiece.

SUMMARY OF THE INVENTION

The desideratum of this invention is to provide a control system for the accommodation of a reasonable number and different types of tools and workpieces to be actuated selectively and finitely from a hand held control device that may be generally of the types disclosed in U.S. Pat. Nos. 3,700,835 and 3,700,836.

Another object of the invention is to provide a control system that enables the operator, as a dentist, to perform his functions more efficiently, with greater speed and with more attention to his patient's needs, without unnecessary distraction and in a less tiring manner, all of which aids in enabling him to perform his tasks more effectively with a minimum of diversion to non-productive movements.

Other objects and features of the invention reside in its versatility of use by enabling the operator to selectively operate any one of a number of tools and workpieces that are simultaneously connected with the circuit of the control apparatus without diverting his attention and losing precious time.

In this regard, a feature and object of the invention is to provide an arrangement of structural details that enables the same to be mounted conveniently within the reach of the dentist for his ease of operation while enabling him to control the operation of the workpieces by means of a hand held, portable control device.

The above description, as well as further objects, features and advantages of the present invention, will be more fully appreciated by reference to the following detailed description of a presently preferred, but nonetheless illustrative embodiment in accordance with the present invention when taken in conjunction with the accompanying drawings wherein:

DESCRIPTION OF THE DRAWINGS

FIG. 3 is a diagram of a fluid operated electrical control for an electrical workpiece, as a motor and the like.

Figure 1:
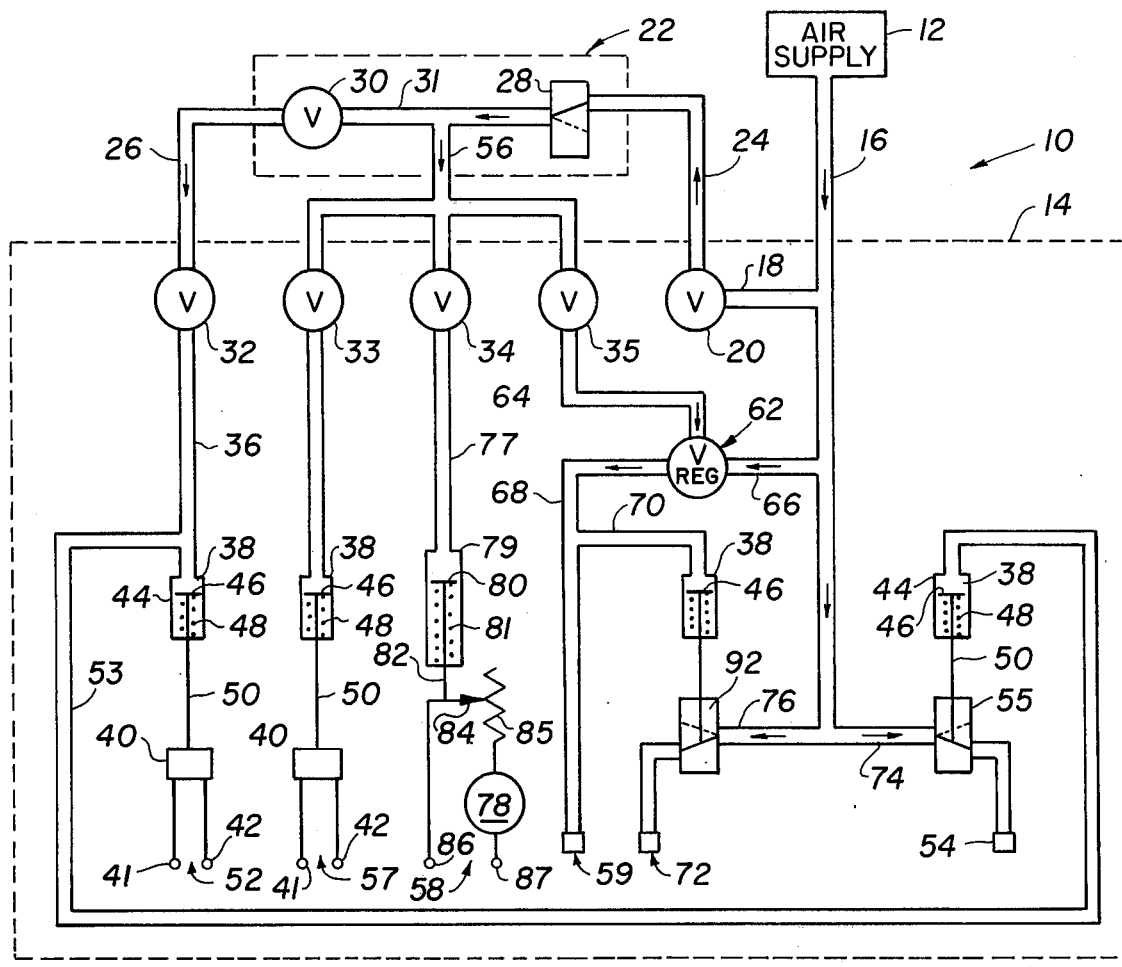
FIG. 1 is a diagram of a control apparatus constructed according to the teaching of the invention.

Referring now to the drawing, the numeral 10 generally identifies the control apparatus having a source of fluid supplied under pressure at 12. The apparatus 10 includes a housing 14 illustrated by broken lines that may be fixedly mounted in any location that is convenient to the operator using the apparatus. Although the apparatus 10 may have general utility, the same is presently disclosed for use by dentists and dental technicians or operators to enable a clearer understanding of the subject matter of the invention. Hence, even though throughout the description reference will hereafter be made to dental use, it is to be understood that the scope of the invention is not to be so limited. Additionally, because modern dental tools or workpieces are air operated, the fluid supply 12 has been conveniently designated as an "air supply". Those skilled in the art will readily recognize that other fluids may be utilized.

The supply 12 of air or other pressurized fluids is connected with the housing 14 in a fluid circuit that is accomplished by a main conduit 16 supplying the air at 18 to a main adjustable flow control valve 20 that is used to regulate the volumetric flow of fluid to a portable hand held control device shown in broken lines and generally identified by the numeral 22. The control device 22 may be of the general appearance of those disclosed in my U.S. Pat. Nos. 3,700,835 and 3,700,836, except that in the present invention such device is adapted to selectively control the flow of fluid and in the manner to be described.

The control device 22 is connected in the fluid circuit with the housing 14 by a flexible conduit or hose 24 at its inlet end and by a similar flexible hose or conduit 26 at its outlet end. To this end, the specific nature of the flexible conduits 24 and 26 is not material. In practice, it has been found that flexible plastic tubing has functioned satisfactorily. This is especially true when the lengths of conduits 24 and 26 are sufficient to enable their deployment and manipulation by the user relative to the housing without limitation as to the fixed location of the housing. Therefore, in practice, it has been found convenient to mount the housing 14 under the dental chair or near the dental unit where it is easily and readily accessible to the operator while the device 22 may be held in the hand of the dentist or operator for finger control of the valves therein.

It will be recognized that the mounting location off the housing 14 should be made to suit the convenience of the dentist or operator. It should suffice to note that without regard to location of the housing 14, the flexible fluid conduits 24 and 26 will permit the hand held control device to be deployed and manipulated in any position by the user. Included within the control device 22 is a pressure responsive, normally closed, fluid valve 28 of conventional design. Being normally closed, the valve 28 blocks the flow of fluid at the inlet conduit 24 through the control device which also includes a shut-off valve 30 that is operable between fully on and fully off positions. A fluid conduit 31 connects the valves 28 and 30 to each other within the control device 22.

The control circuit of the apparatus 10 further includes separate shut-off valves 32, 33, 34 and 35 that may be mounted within the confines of the housing 14 or within a separate control enclosure that may be supported on the back of the dental chair or at some other readily accessible location. These shut-off valves, being of the conventional design, control the flow of fluid from the hand control device 22 to respective fluid actuated output couplings for the actuation of tools and/or other workpieces that may be connected thereto. The flexible connection 26 completes a circuit with the valve 32 which controls the flow along the circuit conduit 36 that terminates in an electrical switch operator 38.

Switch operator 38 controls the operation of a normally open conventional type electrical switch 40 having the electrical leads 41 and 42, here referred to as an outlet coupling, that is connected to an electrical circuit, not shown, and forming no part of the present invention. The switch operator 38 includes a fluid cylinder 44 having a reciprocating piston 46 spring biased at 48 in one direction to prevent the application of closing pressure against the normally open switch 40. However, upon the application of fluid pressure directed into the cylinder 44, the piston is caused to move against the spring 48 to reciprocate its rod 50 to close the switch 40 across the contacts 41 and 42 forming the outlet coupling thereat generally identified by the numeral 52. This results in the actuation of whatever electrically operated tool or workpiece that may be connected at the outlet coupling 52 and to its own source of electricity, not shown, and not forming any part of this invention.

A by-pass conduit 53 is connected in the fluid circuit with the line 36 and includes, in the circuit controlled by the valve 32, an outlet coupling generally identified by the numeral 54. The coupling 54 is controlled by an opeerator 38 having the arrangement of structural details as the operator 38 previously described. However, because the output coupling 54 may be made to control a tool connectable thereto that is fluid actuated, a piston rod 50 thereof is connected with a normally closed fluid control valve 55 of conventional design that is operable between on and off flow positions. When the fluid pressure is applied to the piston 46 of the outlet coupling 54, the same will open the valve 55 to provide a flow of fluid therethrough and to the fluid actuated tool or workpiece that is connected at 54 to control the actuation thereof. For example, the valve to be connected at 54 may provide a cooling spray of water from a supply of water that is not shown because it does not form any part of this invention.

Also flexibly connecting the control device 22 with the housing 14 is a fluid conduit 56 that divides in the housing to connect with each of the shut-off valves 33, 34 and 35. The valve 33 controls the flow of fluid to piston 46 of the electrical outlet coupling generally numbered 57 while the valve 34 controls the flow of fluid to an outlet coupling generally identified as 58. The outlet coupling generally identified as 59 includes within its circuit a regulator valve generally identified as 62.

The regulator valve 62 is connected in a direct fluid circiut with the shut-off valve 35 by conduit 64 while permitting a variable flow of fluid through 62 from the source 12 by the connecting inlet conduit 66. The outlet side of the regulator valve 62 is connected in fluid circuit by the outlet condiut 68 that is joined by a further circuit conduit 70 leading to a switch operator 38 of another output coupling generally identified as 72. The main fluid conduit 16 branches at 74 to supply fluid from the source 12 to the output coupling 54 and at 76 to supply fluid to the outlet coupling 72.

Because the outlet coupling 57, like previously described outlet coupling 52, is intended to control the operation of electrically operated tools or workpieces that may be connected thereto, the control of the electric switches 40 by the fluid circuit must be provided for. In the discussion of the output coupling 52, it was noted how the actuation of the piston 46 causes the initiation of the electrical circuit between the contacts 41 and 42 closing the switch 40. The previously described structure is similarly utilized in the actuation of an electrically driven tool or workpiece that may be connected with the apparatus 10 at the coupling 57.

Figure 3:
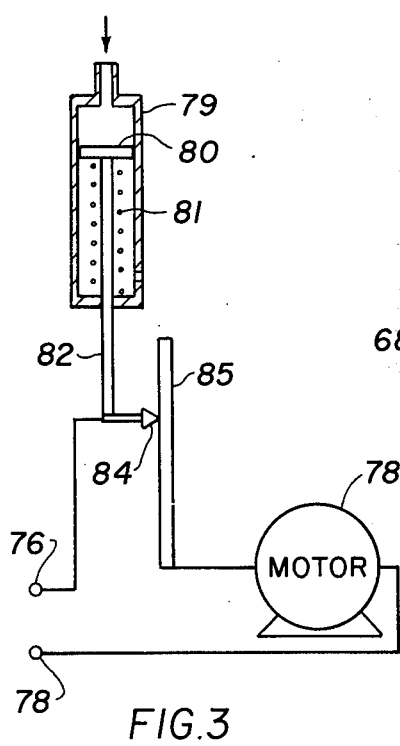
Figure 4:
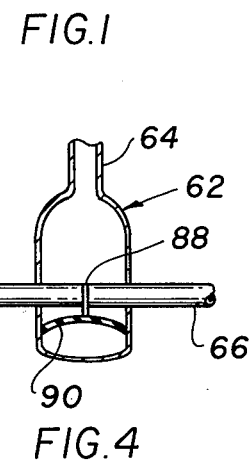
FIG. 4 is a cross-section schematic view of a regulator valve.

When it is desired to finitely control the actuation of such tools or workpieces as electric motors 78 shown connected at the coupling 58 and in greater detail in FIG. 3, fluid is directed by conduit 77 from the shut-off valve 34 to an operator which includes a cylinder 79 having a reciprocable piston 80 biased by a spring 82 to oppose the flow of fluid and its pressure. The piston 82 has electrical contact 84 that is adapted to move along a resistor winding 85 to vary the electrical resistance and flow of operating current to the motor 78 by way of the coupling contacts 86 and 87.

The regulator valve 62 is provided with a movable valve element 88 that is normally biased to close the flow of fluid from the source inlet 66 to the outlet 68. The valve biasing element 90 may be a diaphragm mounted within the regulator valve housing. When fluid flows from the source 12 through the hand control valve 28 along conduits 56 and 64 to the diaphragm 90 of regulator valve 62, an unseating force is applied thereto to correspondingly displace the valve element 88 from between the lines 66 and 68 to thereby variably and selectively control the flow of fluid therebetween. In consequence, the volumetric flow of actuating fluid from the source 12 to the tool or workpiece to be selectively and finitely actuated at the coupling 59 is subject to the hand control effected on valve 28 of the control device 22.

The same finite control of the operation of the motor 78 is effected by the user. By varying the control of the flow of the fluid from the source 12 to the piston 80 of the coupling 58, the operator of the valve 28 on the hand held control device 22 may carefully and selectively actuate the motor or any other electrical workpiece connected thereat at any desired speed. The by-pass conduit 70 being connected in series with the regulator valve 62 similarly subjects the switch operator 38 of the coupling 72 simultaneously with flow to coupling 59 for conjoint operation in the same manner as discussed previously. That is to say, the piston 46 will move in response to the selective operation of the valve 28 to open the pressure regulator 62 to open the valve 92 that opens the flow of fluid from the supply 12 to the tool connected with the coupling 72. Unlike the fluid control valve 92, the valve 55 operates in direct response to the flow of fluid from the source 12 through the hand valve 28 and open valves 30 and 32 acting upon the piston 46 of the coupling 54 simultaneously with electric coupling 52.

Figure 2:
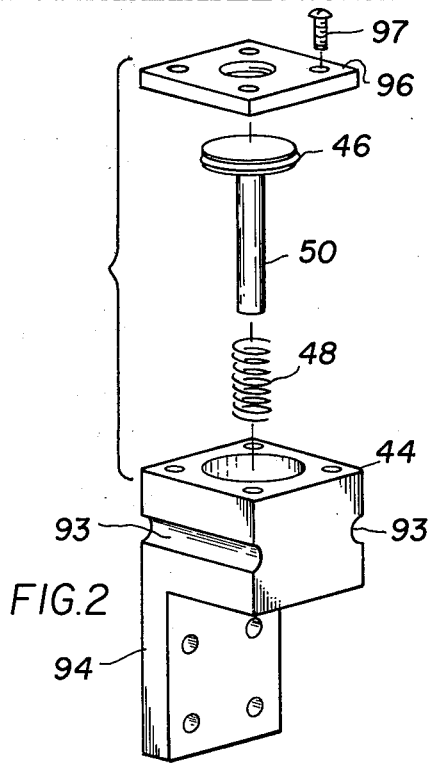
FIG. 2 is an isometric view of an operating cylinder included as a part of the control apparatus.

Enlarged details of the switch operator 38 are shown in FIG. 2. It will be clear that it is not material whether the operators 38 are used as drivers for the electric switches 40 or as actuators for the fluid control valves 55 and 92. In either manner of use, the same will function in response to the application of fluid pressure applied thereto. The switch operators 38 are adapted to be mounted within the housing 14 by securing the same thereto by screws or other fastening means (not shown) extending through the side grooves 93 in the bracket 94. The outlet couplings 52, 54, 57, 58, 59 and 72 may be mounted on an interior wall of the housing and exposed to the exterior side of the housing for connection to an already existing dental unit having dental tools and other workpieces. A cover plate 96 may be used to close the top of the cylinder 44 by the application of fastening means or screws 97.

In operation, the control of electrically operated tools or workpieces may be effected by selectively connecting the same into the circuit of the apparatus 10 at the output couplings 52 and 57. The control of fluid actuated tools or workpieces may be effected by selectively connecting the same into the circuit of the apparatus at couplings 54, 59 and 72. In such instances, the coupling 54 may be used to control the flow of coolant water spray to a dental handpiece that may be selectively connected for simultaneous operation at the coupling 59. Alternatively, while the dental handpiece is being selectively and variably controlled at coupling 59, an electrically operated water coolant spray tool (not shown) may be connected at coupling 52 for simultaneous and selective control.

In the operation of dental equipment, it is convenient to provide a separate central slave control unit to which many tools or workpieces may be simultaneously connected and ready for use. This is accommodated in the present apparatus 10 wherein such separate central slave control unit (not shown) is conveniently connected to the apparatus 10 to be controlled thereby at the outlet coupling 72. The outlet coupling 72 being a full pressure line, that is to say, it receives full fluid pressure directly from the source 12, may be used, when necessary, to control switches, valves and the like in the separate central slave control unit. Because the slave unit may have a plurality of tools and workpieces simultaneously connected to it, it is desirable to have separate valves, switches, and the like for each such tool or workpiece. By the operation of such switches, valves and the like, the desired tool or workpiece may be enabled to operate. In this case, the flow of fluid through the coupling 72 to all of the switches or valves or the like simultaneously will actuate the same to enable their usage. Simultaneously, the described slave unit may also be connected to the outlet coupling 59 which receives a variable controlled flow of fluid and which directs such controlled fluid flow to the particular selected tool or workpiece of the slave unit.

Hence, while the flow from the outlet 72 to the particular selected tool or workpiece at the slave unit will cause the operation of the switch or valve to the selected tool or workpiece, the flow of fluid from the outlet 59 to the same workpiece will control the speed of operation of such workpiece. Thus, it is possible that the outlet 59 may be used directly with any one tool or workpiece that may be connected with the same or it may be used in combination with the outlet coupling 72 for connection with a slave unit having a plurality of tools and workpieces that are ready for simultaneous usage.

When the main adjustable flow control valve 20 is opened, a desired amount of fluid will flow from the supply 12 to the hand held control device 22 where its flow is infinitely controlled by finger pressure against the valve 28 thereof. If the valve 30 of the device 22 is opened, fluid will flow along the condiut 26 to the valve 32. Thus, by selective operation of the valve 30 and valve 28, the control of fluid may be directed along both the lines 56 and 26. When directed along the line 26, the valve 32 may be opened to utilize either the electrical coupling 52 thereof or the fluid actuated coupling 54 thereof, depending upon whether the tool or workpiece is electrically operated or fluid operated.

Thus, the user of the present apparatus 10 has the ability to operate a tool either electrically or by fluid actuation, or both. If the valves 30 and 32 are open and additionally, the valve 35 is open while the valves 33 and 34 are closed, fluid will flow not only to the couplings 52 and 54 for selective use thereof, but also to the regulator valve 62 to control the fluid flow from the main supply 12 through such valve. Inasmuch as the flow of fluid from the supply 12 is constant along the line 16, fluid will flow to the regulator 62 by way of the line 66 and from there to the by-pass 70.

If a fluid actuated tool or workpiece is connected to the outlet 59, the same may be utilized simultaneously with whatever tools or workpieces may have been connected to either the couplings 52 and/or 54. Hence, it is possible to operate a dental drill by means of fluid pressure at the coupling 59 while simultaneously supplying a cooling supply of fluid from 12 by way of line 74 to the coupling 54 by the simple actuation of the valve 28 at the hand control device 22. The regulated flow of fluid to the coupling 59 as controlled by the valve 28 will control the speed of the tool connected to the coupling 59 while simultaneously controlling the flow of fluid from the supply 12 to the coupling 54. Thus, it will be recognized that one or more tools connected in the circuit may be finitely controlled by the simple application of hand pressure to the switch 28 on the portably hand held control device 22.

In like manner, if all or some of the valves 32, 33, 34 and 35 are opened, their respective couplings will be subjected to the finger pressure exerted by the operator on the hand held valve 28. In this way, it is possible to select any one or any combination of tools and/or workpieces for simultaneous operation and to control their operation in accordance with the needs and the desire of the operator of the present apparatus 10. When a fluid actuated tool or workpiece is connected at either coupling 54 or 72, the movement of the piston 46 of the respective coupling will respond in accordance with the operation of the hand held valve 28. As fluid is permitted to pass through the valve 28 from the supply 12, the piston 46 will be depressed against a spring 48 thereby moving either the valve element 55 or 92 from its closed position to its opened position. The movement of the valves 55 and 92 are subject to the control of the valve 28. Thus, any tool connected at the couplings 54 or 72 will receive a flow of fluid from the supply 12 as controlled by the operator at the valve 28.

The present disclosure has been made in connection with the supply of air as the operating fluid medium only because fluid conduits are shown to be arranged in a single direction of flow. In the event the conduits include return fluid conduits to the supply 12 or a reservoir (not shown), it will be realized that the present invention may be utilized in connection with liquids as well as gaseous fluids. Hence, it is within the scope of the invention not to be limited to the specific use of a gaseous fluid medium.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. In a dental apparatus for controlling a dental workpiece,
a plurality of output couplings to which dental workpieces may be selectively connected,
a source of fluid under pressure for operating the workpieces connected to said couplings,
a hand held assembly having a portable valve that is hand operated to selectively vary the flow of fluid therethrough,
flexible fluid conduit means connecting said portable valve between said output couplings and said source of fluid to enable the unrestricted movement of said portable valve,
variable valve means connected with said portable valve and between certain selected ones of said plurality of output couplings and said fluid source to variably control the flow of fluid from said source to said selected output couplings in response to the selected hand operation of said portable valve,
and operable valve means between said variable valve means and at least one of said certain selected output couplings operable in response to the operation of said portable valve to control the operation of a workpiece connected with said one output coupling.

2. In a dental apparatus as in claim 1,
a shut-off valve means between said source of fluid and each of said output couplings to open and close the flow of fluid therebetween.

3. In a dental apparatus as in claim 2,
said portable valve including shut-off valve means to open and close the flow of fluid therethrough to certain of said output couplings.

4. In a dental apparatus as in claim 1,
and shut-off valve means on said hand held assembly and in series with said portable valve to open and close the flow of fluid from between said portable valve and certain of said output couplings.

5. In a control system for an air actuated dental workpiece,
a source of pressurized air,
a plurality of output couplings to which dental workpieces are connected for actuation by the air,
conduit means connecting said output couplings and air source in circuit to conduct air therebetween,
a portable hand held control device in said circuit between said output couplings and said source,
said conduit means including flexible conduit means to enable unrestricted portable movement of said control device relative to said source and said output couplings,
a valve in said control device selectively hand operable to control the actuation of the dental workpieces,
variable valve means connected with said hand operable valve to variably control the flow of air to certain of said output couplings to thereby control the operation of workpieces connected therewith,
and valve means operable in said circuit between said variable valve means and at least one of said output couplings to open and close the flow of air to said one output coupling in response to control of air flow by said variable valve means and being between said hand operable valve to open and close the flow of air to another output coupling in response to the operation of said hand operable valve.

6. In a control system as in claim 5,
and air actuated cylinders in said circuit and associated with certain of said plurality of output couplings and including piston means movable in response to the selective operation of said selectively hand operable valve.

7. In a control system as in claim 6,
an electrically operated workpiece connected with at least one of said plurality of output couplings,
electrical contact means between said workpiece and movable piston to vary the electrical operation of the workpiece in response to the movement of said piston.

8. In a control system as in claim 6,
a housing fixedly mounting said output couplings and associated cylinders,
and said flexible conduit means connecting said control device for portable manipulation and selective operation between said housing and air source.

9. In a control system as in claim 8,
and operable on-off valve means between said control device and said output couplings to selectively open and close the flow of air therebetween.

* * * * *